United States Patent [19]
Fulwyler

[11] 3,989,381
[45] Nov. 2, 1976

[54] OPTICAL CHAMBER WITH SPHERICAL REFLECTIVE PORTION AND APPARATUS EMPLOYING SAME

[75] Inventor: Mack J. Fulwyler, Los Alamos, N. Mex.

[73] Assignee: Coulter Electronics, Inc., Hialeah, Fla.

[22] Filed: May 5, 1975

[21] Appl. No.: 574,270

[52] U.S. Cl. .................................. 356/39; 356/103
[51] Int. Cl.² .................. G01N 33/16; G01N 21/00
[58] Field of Search .............................. 356/39–42, 356/103–104, 197

[56] References Cited
UNITED STATES PATENTS
3,869,208   3/1975   Lorenz ............................. 356/103

FOREIGN PATENTS OR APPLICATIONS
514,653   11/1939   United Kingdom ................. 356/103

OTHER PUBLICATIONS
Jenkens et al, "Fundamentals of Optics," McGraw-Hill 1950, pp. 37, 91.

Primary Examiner—John K. Corbin
Assistant Examiner—Wm. H. Punter
Attorney, Agent, or Firm—Silverman & Cass, Ltd.

[57] ABSTRACT

An optical chamber for use in an apparatus for measuring characteristics of small particles such as blood cells while the particles are suspended in a liquid includes a housing which defines the optical chamber. An entrance and exit are formed in the chamber for allowing entry and exit of the particle suspending liquid. The chamber itself is formed to allow passage of the particle suspending liquid therethrough in a thin stream with the particles in the stream passing through the chamber in sequence. A portion of the housing is formed from light transmitting material for allowing a beam of light to be transmitted into the chamber where it intersects the thin stream of particle suspending liquid at a junction point and produces resultant light upon intersecting said particles. A spherical shaped portion is formed in the housing and is concave into the chamber with the radial center of the spherical shaped portion located substantially at the junction point. The concave surface is reflective to reflect the resultant light coupled thereto. An apparatus including the optical chamber is also disclosed.

4 Claims, 2 Drawing Figures

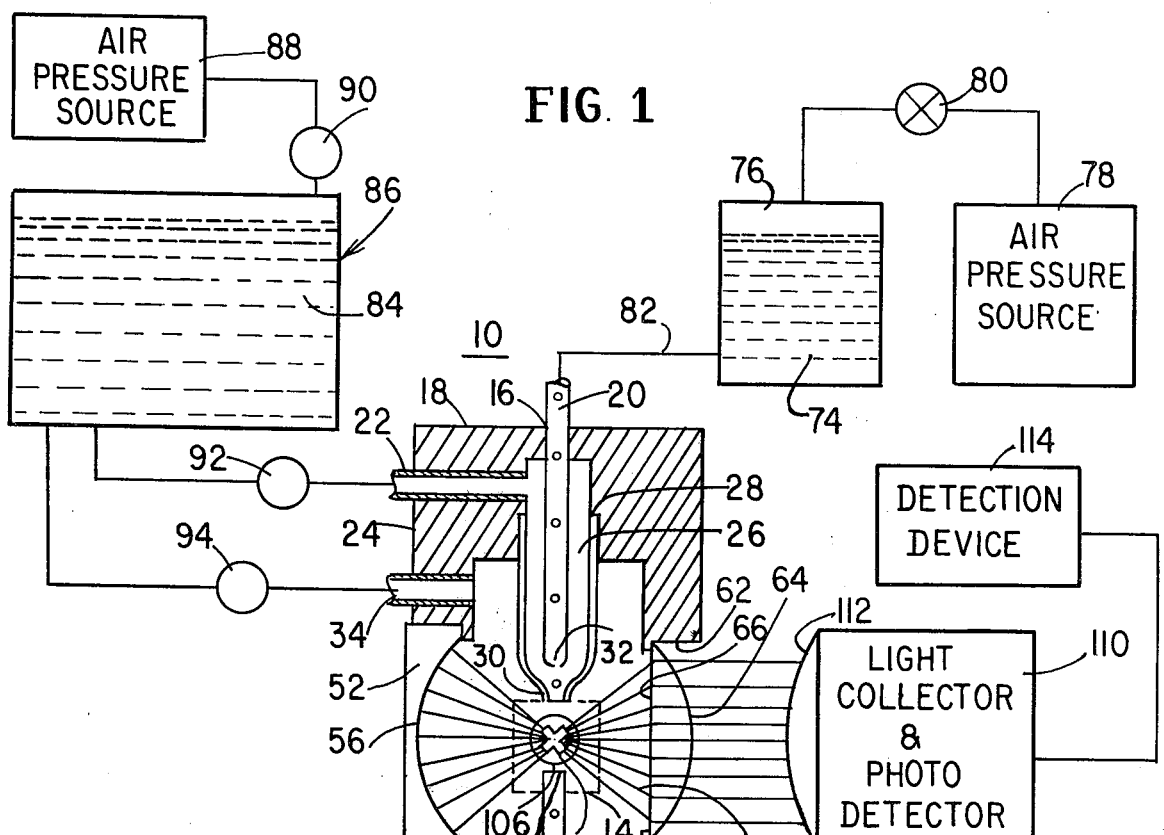
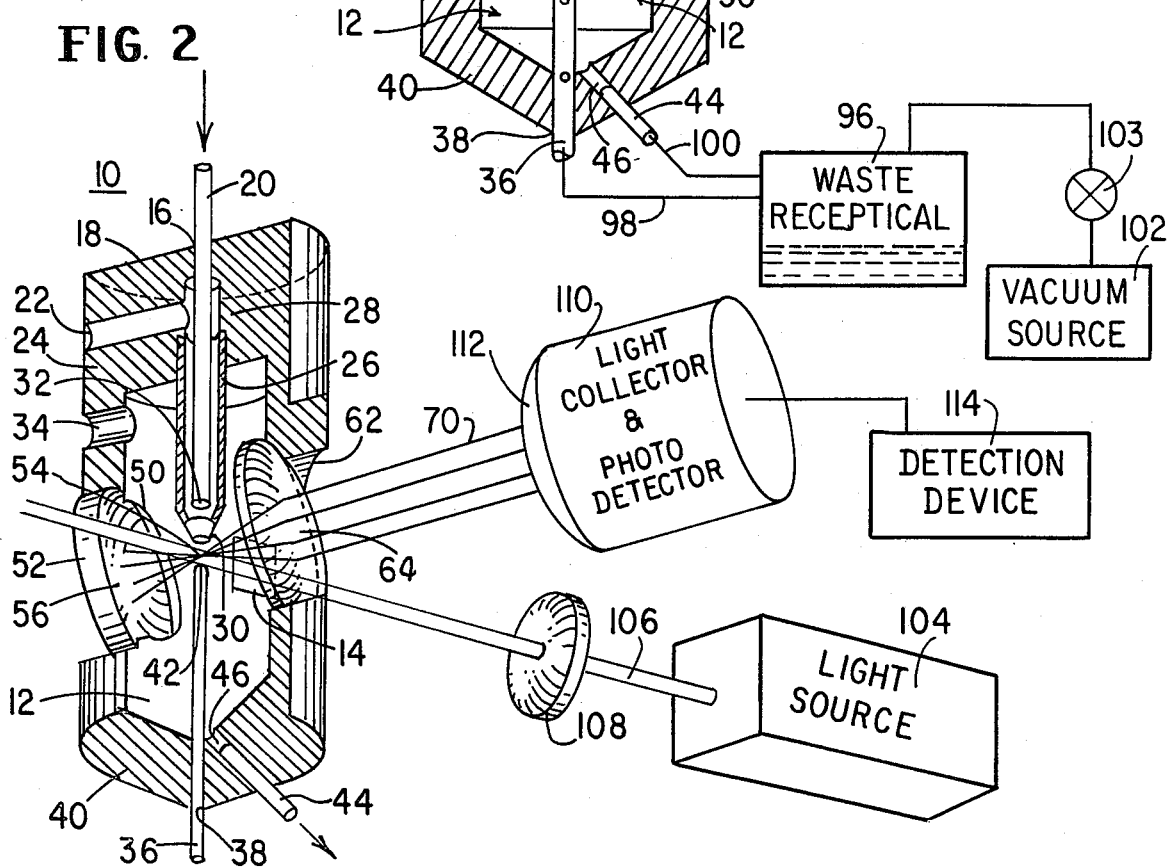

OPTICAL CHAMBER WITH SPHERICAL REFLECTIVE PORTION AND APPARATUS EMPLOYING SAME

BACKGROUND OF THE INVENTION

This invention relates to photoanalysis apparatus which measure the amount of resultant light produced by passage of particles in a sample of fluid through a beam of light.

In a photoanalysis apparatus as presently constructed, a fluid sample containing particles to be detected is passed through an optical chamber generally in a thin stream so that the particles pass through the chamber in succession. A beam of light is passed through the chamber in a direction perpendicular to the passage of the fluid sample. When a particle in the fluid sample intersects the light beam, light is scattered and/or fluorescent light is generated. The scattered and/or fluorescent light, hereinafter termed resultant light, may be detected by photodetectors positioned off axis with respect to the beam of light projected through the fluid and perpendicular to the axial direction of flow of the fluid. That is, the source of light and the optical detectors are generally positioned in a common plane but are at angles other than zero with respect to one another.

In the type of apparatus described, a minute amount of resultant light generally is available because the particles to be detected are very small, intersecting only a small amount of light in the light beam. In order to detect the resultant light either a very high intensity light source must be used in order to increase the amount of resultant light produced or very sensitive photodetectors must be employed. In many applications both a high intensity light source such as a laser and very sensitive photodetectors are employed.

High intensity sources which may be employed are expensive and often have a short useful life. Sensitive photodetectors such as noted above, in addition to being very sensitive to small amounts of illumination, are also extremely sensitive to environmental conditions. That is, they respond to a great many different types of noise signals in the same manner as they would respond to very small amounts of illumination. The circuitry employed in association with these highly sensitive photodetectors must be very sophisticated, and therefore very expensive in order to discriminate between signals generated due to noise and signals generated due to low levels of illumination.

A number of arrangements have been employed in order to eliminate the need for very high intensity light sources and very sensitive photodetectors. In one such arrangement, a mirror is located outside of and on one side of the optical chamber, and is aligned with the optical axis of the photodetectors employed. Part of the resultant light produced by passage of a particle through the optical chamber will be reflected by the mirror to the photodetectors thereby increasing the amount and/or intensity of resultant light they receive and detect. In another arrangement, a number of mirrors are positioned outside of the optical chamber and substantially surround the chamber, except, of course for the portions through which the incident beam of light passes. Almost all of the resultant light produced by passage of a particle through the incident beam is reflected by these mirrors. The mirrors are formed such that they will reflect substantially all of the light received in a particular narrow beam onto the photodetectors.

Although the mirror arrangements noted in the preceding paragraph appear to be quite successful in allowing a reduction of the light source intensity and/or sensitivity of the photodetectors employed, they have certain disadvantages. Foremost among the disadvantages appears to be the presence of interfaces which can produce a reduction in light intensity, a distortion of the resultant light, and/or an increase in the noise generated within the system. Examples of interfaces include the interface produced between the fluid in the optical chamber and the material forming the optical chamber; the interface produced by the material forming the optical chamber and the air between the chamber and the mirror; and the interface formed by all three of the fluid, optical chamber material and air between the chamber and the mirror.

SUMMARY OF THE INVENTION

In practicing this invention an apparatus is provided for measuring optical characteristics of small particles such as blood cells while the particles are suspended in a liquid. The apparatus includes a source of light for developing a light beam. A housing in the apparatus defines an optical chamber. The housing includes a portion for allowing transmission of the light beam from the source into the chamber. The housing also includes a mirrored spherical shaped portion with the radial center of this spherical shaped portion, that is the center of the sphere from which the spherical shaped portion would be removed, intersecting the light beam in the optical chamber at a junction point. Structures are provided for moving the particle suspending liquid through the optical chamber in a thin stream so as to cause the particles in the stream to pass in sequence through the junction point. Passage through the junction point produces either light scatter and/or fluorescense, previously defined as resultant light. A photoresponsive pick-up element is aligned with the junction point and positioned substantially opposite to the mirrored surface of the spherical portion for detecting the resultant light directly received and reflected by the light reflective surface. The detected light is employed to detect and identify the particles passing through the junction point.

The housing forming the optical chamber is itself considered as being within the scope of this invention.

BRIEF DESCRIPTION OF THE DRAWINGS

FIG. 1 is a combined schematic diagram and plan view, partially in section, of the photoanalysis apparatus and optical chamber of this invention;

FIG. 2 is a combined schematic diagram and perspective view, partially in section, of certain portions of the apparatus shown in FIG. 1.

DETAILED DESCRIPTION OF THE PREFERRED EMBODIMENT

Referring to the Figures, there is shown a housing 10 forming a central opening and defining an optical chamber 12. Housing 10 and chamber 12 generally may be formed in any configuration such as, for example, a cylindrical, square or rectangular configuration. In the embodiment shown, housing 10 and optical chamber 12 are both generally cylindrical. Housing 10 is formed from a material which is impervious to most chemicals. Glass, metal, or a plastic which does not deteriorate in response to most chemicals is generally employed for forming housing 10. Although glass or plastic are preferably employed, it is to be understood that materials such as stainless steel may be employed if desired for forming housing 10. If glass or a clear plastic is used in forming housing 10, the housing wall will transmit light beams therethrough as in necessary for reasons explained in greater detail subsequently. If, however, a material such as stainless steel is employed for housing 10, a portion of the housing shown via dotted lines and identified by the reference number 14; and a portion radially opposite dotted line portion 14 of the housing must be formed from a material which transmits light therethrough.

An entry aperture 16 is formed in top wall 18 of housing 10. A liquid sample entry tube 20 is secured in aperture 16 and extends a substantial distance into optical chamber 12. A second entry aperture 22 is formed in the side wall 24 of housing 10. A sheath flow tube 26 is secured in optical chamber 12 coaxial with the axis of liquid sample tube 20. The entry end 28 of sheath flow tube 26 communicates with aperture 22 and the exit end 30 is positioned slightly beyond exit end 32 of liquid sample tube 20 interior to chamber 12. A third entry aperture 34 is formed in side wall 24 of housing 10 and the third entry aperture 34 communicates directly with optical chamber 12.

A liquid sample exit tube 36 is secured in an aperture 38 formed in bottom wall 40 of housing 10. Liquid sample exit tube 36 extends into optical chamber 12 with its axis aligned with the axis of liquid sample entry tube 20. An entry end 42 of liquid sample exit tube 36 is positioned closely adjacent to exit end 30 of sheath flow tube 26. A sheath fluid exit tube 44 is secured in an exit aperture 46 formed in bottom wall 40 of housing 10 for allowing exit of the sheath fluid accumulated within optical chamber 12.

Side wall 24 of housing 10 has an aperture 50 formed therein with a spherical shaped portion 52 secured in aperture 50. Spherical shaped portion 52 is concave inward towards the center of optical chamber 12 with the radial center of the sphere from which portion 52 is taken, being located at a junction point 54 within chamber 12. The concave surface 56 of spherical shaped portion 52 is reflective for reflecting light therefrom. In the preferred embodiment, spherical shaped portion 52 is formed from glass and surface 56 is mirrored. In an alternate embodiment, spherical shaped portion 52 may be formed from a stainless steel member with surface 56 machined to be highly reflective. The radial center of portion 52 and the radius of curvature of the surface 56 of spherical shaped portion 52 are selected such that any resultant light emanating from junction point 54 and traveling directly to surface 56 will strike surface 56 at an angle which is perpendicular to the surface at the point of impact. Consequently the light reflected will leave surface 56 at an angle which is perpendicular to the surface at the point of departure and travel back to and through junction point 54 emanating therefrom in a conical shaped volume represented by the lines 58.

Another, or second, aperture 62 is formed in side wall 24 substantially radially opposite to spherical shaped portion 52. A collection lens 64 is secured in aperture 62. Lens 64 is selected and mounted in aperture 62 such that its focal point will be at substantially the same location as junction point 54 of spherical shaped portion 52. Collection lens 64 is circular so that the conical shaped volume indicated by lines 58 and representing the light reflected from surface 56 through junction point 54 will strike the inner surface 66 of lens 64 thus receiving and collecting all of the resultant light reflected from surface 56. Lens 64 is ground such that all of the light beams striking surface 54 and emanating substantially from junction point 54 will be refracted so that they exit collecting lens 64 at outer surface 68 thereof as parallel beams of light represented by lines 70.

An apparatus for measuring characteristics of small particles such as blood cells while the particles are suspended in a liquid, which includes housing 10 defining an optical chamber 12, is shown in FIG. 1. In that apparatus, a liquid suspension of particles 74 is shown contained in a sample vessel 76 under pressure supplied by an air pressure source 78 through a pressure regulator 80. The liquid suspension of particles is coupled to liquid sample entry tube 20 via a conduit represented by line 82.

A particle free sheath liquid 84 is contained in a sheath liquid vessel 86 which is also maintained under pressure by an air pressure source 88 through pressure regulator 90. The sheath liquid in the vessel 86 is coupled to second entry aperture 22 via conduits and a flow regulating device 92 which regulates the amount of sheath fluid provided and the rate at which it is provided. Sheath fluid entering second entry aperture 22 passes into sheath flow tube 26. The sheath fluid in vessel 86 is also coupled to third entry aperture 34 via conduits and a flow regulator 94 which operates in substantially the same manner as regulator 92. The sheath fluid entering third aperture 34 is employed to fill the optical chamber 12.

A waste receptacle 96 is provided for receiving particles in suspension which have passed through optical chamber 12. Waste receptacle 96 communicates with liquid sample exit tube 36 via a conduit represented by line 98 and with sheath fluid exit tube 44 via a conduit represented by line 100. Waste receptacle 96 is subjected to a source of vacuum 102 which is coupled to waste receptacle 96 via a vacuum regulator device 103 in order to draw the passed particles and sheath flow into the receptacle.

A light source 104 is shown in FIG. 2. In the preferred embodiment, light source 104 is a laser. The beam 106 developed by laser light source 104 is shown in side view in FIG. 2 and is shown looking directly into the beam 106 in FIG. 1. Light source 104 and light beam 106 are positioned such that beam 106 passes through the optically transmitting material portion 14 in side wall 24 of housing 10 and into optical chamber 12. The beam 106 passes between exit end 30 of tube 26 and entrance end 42 of exit tube 36, intersecting junction point 54. One or more lenses such as is represented by lens 108 may be positioned between light source 104 and housing 10 in order to reduce the diameter of beam 106, collimate the beam and cause it to converge substantially at junction point 54.

A combined light collector and photodetector 110 is shown aligned with the optical axis of collection lens 68. Light collector and photodetector 110 includes a collection lens 112 and a photodetector 110a (not shown). Light beams such as 70 coupled from lens 64 are collected by lens 112 and coupled to the photodetector 110a. Photodetector 110a will respond to light coupled thereto and develop an electrical signal which is coupled to a detection device 114. The detection device 114 may be a counter or some other device which provides a positive indication of the detection of a particle and records the same.

In operation, optical chamber 12 is filled with a sheath fluid flowing from sheath vessel 86 to waste receptacle 96. The particles in a liquid suspension are coupled from sample vessel 76 through liquid sample entry tube 20 into optical chamber 12 at tube exit 32 closely adjacent to junction point 54. A continuous flow of sheath liquid coupled from sheath reservoir 86 is introduced from tube 26 and flows coaxially around tube 20. This sheath liquid travels at a substantially greater velocity than the sample suspension liquid. As the sample suspension liquid exits tube 20 and contacts the sheath liquid its velocity increases to that of the sheath liquid 84 and it is reduced in diameter. This results in a very thin stream of particles in suspension passing through junction point 54 and from junction 54 to exit tube 36. The thin stream causes the particles to pass through junction point 54 in sequence. As each particle passes through laser beam 106 which converges at junction point 54, it will cause a portion of the laser beam to scatter and/or the particles to fluoresce due to the presence of fluorescent stain or other fluorescent tag. Part of the scattered light waves and/or fluorescent light waves which are defined as resultant light, will emanate from junction point 54 and travel to surface 56 of spherical shaped portion 52. When this part of the resultant light reaches surface 56 it will be reflected back on itself. The reflected resultant light will pass through point 54 as explained earlier and, along with another portion of the resultant light will be passed in a conical shaped volume 58 to collection lens 64. Collection lens 64, because its focal point is at junction point 54, will collect substantially all of the light waves emanating from point 54 and refract the light beams into parallel aligned light beams represented by lines 70. These light beams will be coupled to light collector and photodetector 110 causing the photodetector therein to produce an electrical signal which is coupled to detection device 114. Detection device 114 will register a detection of the particle and, if fluorescent signals have been detected, can also determine certain characteristics of the particle.

Because the mirrored surface of sphere shaped portion 52 is directly in contact with the sheath fluid in optical chamber 12, which is where the resultant light is produced, there are no water/glass, glass/air or water/glass/air interfaces through which the resultant light must pass before it is accumulated by a reflector, and there is a reduction in the amount of intensity loss, distortion and resultant noise. Furthermore, surface 66 of collection lens 64 is also in contact with the sheath fluid in optical chamber 12 so that there are no interfaces through which the resultant light must pass before it is collected by a collection lens. This further reduces the amount of light intensity loss, distortion and/or system noise. Lastly, the use of a refraction type lens 64 whose focal point is the point from which the resultant light signals emanate results in a series of parallel and aligned light rays emanating from the collection lens. It is well known that alignment of filters, lenses and pinholes, all apparatuses which may be used in association with light collector and detector 110 and the detection device 114, is greatly simplified when the light to be detected emerges from its sources, in this case collection lens 64, as a parallel beam.

While the present invention has been described by a reference to a specific example, it is to be understood that modifications may be made by those skilled in the art without actually departing from the invention shown and described herein. It is therefore intended that the appended claims cover all variations that fall within the scope and spirit of this invention.

What is desired to secure by Letters Patent of the United States:

1. An apparatus for measuring characteristics of small particles such as blood cells while the particles are suspended in a liquid including in combination:

a source of light for developing a light beam;

a housing forming an optical chamber and including means for allowing transmission of said light beam from said source into said chamber, said housing including a substantially spherical shaped portion with the center of said spherical shaped portion substantially at the point of convergence of said light beam in said chamber, said spherical shaped portion having a light reflective surface formed thereon for reflecting light therefrom, means for moving the particle suspending liquid through said chamber in a thin stream to cause particles therein to pass in sequence through said light beam one by one at a junction and to produce resultant light by passage through said beam;

at least one photoresponsive pick-up element aligned with said junction and positioned substantially opposite said spherical shaped portion for detecting the resulting light produced by said particles and the resultant light reflected by the light reflective surface of said spherical shaped portion whereby said particles are detected and identified, said center of said spherical shaped portion and the radius of curvature of said spherical shaped portion are selected such that the resultant light produced by particles passing through said junction which strikes said reflected surface strikes same perpendicular to said reflective surface and is reflected back substantially to the junction.

2. An apparatus for measuring characteristics of small particles such as blood cells while the particles are suspended in a liquid including in combination:

a source of light for developing a light beam;

a housing forming an optical chamber and including means for allowing transmission of said light beam from said source into said chamber, said housing including a substantially spherical shaped portion with the center of said spherical shaped portion substantially at the point of convergence of said light beam in said chamber, said spherical shaped portion having a light reflective surface formed for reflecting light therefrom, means for moving the particle suspending liquid through said chamber in a thin stream to cause particles therein to pass in sequence through said light beam one by one at a junction and to produce resultant light by passage through said beam;

at least one photoresponsive pick-up element aligned with said junction and positioned substantially opposite said spherical shaped portion for detecting the resultant light produced by said particles and the resultant light reflected by the light reflective surface of said spherical shaped portion whereby said particles are detected and identified;

collection means, including a collection lens constructed and arranged to collect said resultant light produced and said resultant light reflected and to direct said collected light to said photoresponsive device in parallel beams, said collection lens forming a portion of said housing and said photoresponsive device being positioned outside of said housing and aligned with said collection lens optical axis, said collection lens being positioned on said housing such that the focal point thereof is substantially at said junction for maximizing collection of said resultant light.

3. An optical chamber for use in an apparatus for measuring characteristics of small particles such as blood cells while the particles are suspended in a liquid characterized by:

a housing defining said optical chamber;

entrance means formed in said housing for allowing entry of said particle suspended liquid;

exit means formed in said housing for allowing exit of said particle suspended liquid;

said chamber being formed to allow passage of said particle suspending liquid therethrough in a thin stream with particles in said stream passing therethrough in sequence;

light transmitting means forming a portion of said housing for allowing a beam of light to be transmitted into said chamber, said light beam intersecting said thin stream of particle suspended liquid and producing resultant light upon intersecting said particles;

a spherical shaped portion forming a portion of said housing, said spherical shaped portion being concave into said chamber with the center of said spherical shaped portion located substantially at the intersection point of the center of said thin stream of particle suspended liquid and said light beam, the concave surface of said spherical shaped portion in said chamber being reflective to reflect resultant light coupled thereto, said radial center of said spherical shaped portion and the radius of curvature of said spherical shaped portion are selected such that resultant light striking said reflective surface strikes same perpendicular to said surface and is reflected back substantially to the point of intersection of said light beam and center of said thin stream;

light collection means forming a portion of said housing and aligned with said intersection point and said spherical shaped portion for collecting the resultant light produced by and the resultant light reflected through said intersection point and for directing said collected light exterior to said housing.

4. An optical chamber for use in an apparatus for measuring characteristics of small particles such as blood cells while the particles are suspended in a liquid characterized by:

a housing defining said optical chamber;

entrance means formed in said housing for allowing entry of said particle suspended liquid;

exit means formed in said housing for allowing exit of said particle suspended liquid;

said chamber being formed to allow passage of said particle suspending liquid therethrough in a thin stream with particles in said stream passing therethrough in sequence;

light transmitting means forming a portion of said housing for allowing a beam of light to be transmitted into said chamber, said light means intersecting said thin stream of particle suspended liquid and producing resultant light upon intersecting said particles;

a spherical shaped portion forming a portion of said housing, said spherical shaped portion being concave into said chamber with the center of said spherical shaped portion located substantially at the intersection point of the center of said thin stream of particle suspended liquid and said light beam, the concave surface of said spherical shaped portion in said chamber being reflective to reflect resultant light coupled thereto;

a collection lens secured to and forming a part of said chamber housing, said collection lens being positioned thereon such that the focal point thereof is substantially at the junction of the center of the thin stream of particle suspending liquid and intersecting light beam for maximizing collection of light scattered thereat and reflected therethrough from said reflective surface, said collection lens being constructed and arranged to direct said collected light external to said housing in parallel beams.

* * * * *